United States Patent [19]

Brewster et al.

[11] Patent Number: 5,128,123
[45] Date of Patent: Jul. 7, 1992

[54] CLEAR COSMETIC STICKS

[75] Inventors: David A. Brewster, Shelton; Matthew Kuznitz, Branford; Joseph R. Faryniarz, Oxford, all of Conn.

[73] Assignee: Chesebrough-Pond's USA Co., Division of Conopco, Inc., Greenwich, Conn.

[21] Appl. No.: 652,962

[22] Filed: Feb. 8, 1991

[51] Int. Cl.$^5$ ............... A61K 7/32; A61K 31/13
[52] U.S. Cl. ...................... 424/65; 514/715; 514/716; 424/78.02; 424/401
[58] Field of Search ............ 424/78, 83, 401, 64, 424/65, 73, 81, 568

[56] References Cited

U.S. PATENT DOCUMENTS

| | | | |
|---|---|---|---|
| 2,900,306 | 8/1959 | Slater | 424/65 |
| 3,579,465 | 5/1971 | Schmolka | 252/315.1 |
| 3,740,421 | 6/1973 | Schmolka | 424/65 |
| 4,217,250 | 8/1980 | Holzner | 512/2 |
| 4,226,889 | 10/1980 | Yuhas | 424/59 |
| 4,290,904 | 9/1981 | Poper et al. | 252/118 |
| 4,504,465 | 3/1985 | Sampson et al. | 424/65 |
| 4,678,664 | 7/1987 | Schmolka | 424/65 |
| 4,702,916 | 10/1987 | Geria | 424/400 |
| 4,759,924 | 7/1988 | Luebbe et al. | 424/42 |
| 4,948,578 | 8/1990 | Burger et al. | 424/68 |
| 4,954,332 | 9/1990 | Bissett et al. | 424/64 |

FOREIGN PATENT DOCUMENTS 0137173  4/1985  European Pat. Off. .

OTHER PUBLICATIONS

BASF Bulletin (1987), Pluronic & Tetronic Block Copolymer Surfactants "Applications of Pluronic Polyols in the Cosmetic Industry" by Schmolk; American Perfumer and Cosmetics, vol. 82, Jul. 1967; pp. 25-30.

*Primary Examiner*—Thurman K. Page
*Assistant Examiner*—Sally Gardner
*Attorney, Agent, or Firm*—Milton L. Honig

[57] ABSTRACT

A clear cosmetic stick is provided whose composition includes from about 10 to 90% of a polyhydric alcohol, from about 1 to about 40% of a soap, from about 1 to about 40% of an alkoxylate copolymer having the formula:

$$[A-CH_2CH_2-A]_f[(C_2H_4O)_a(C_3H_6O)_b(C_2H_4O)_c(C_3H_6O)_d]_e[H]_g$$

wherein
A is nitrogen;
a, b, c and d are independently selected integers ranging from 0 to 200 with the proviso that the sum of a, b, c and d is at least about 50;
e is an integer from 1 to 4;
f is an integer from 0 to 1-;
g is an integer from 0 to 4;
and a clarifying agent which is a basic amine present in an effective amount to maintain stick clarity.

16 Claims, No Drawings

CLEAR COSMETIC STICKS

BACKGROUND OF THE INVENTION

1. Field of the Invention

The invention relates to cosmetic compositions in the form of sticks having excellent clarity, stability and mildness.

2. The Related Art

Cosmetic compositions in stick form are well-known. These compositions may be employed as deodorants, antiperspirants, lipsticks and the like. Efforts have been made in the art to provide such compositions with skin mildness properties and with clarity for improved aesthetics.

U.S. Pat. No. 4,759,924 (Luebbe et al) discloses a transparent soap gel cosmetic stick stated to possess good cosmetics as well as clarity. Deodorant formulas are described therein containing a polyhydric alcohol, soap, an ethyoxylated-propoxylated fatty alcohol and a deodorant active, such as Triclosan, in an aqueous carrier. Similar compositions are reported in U.S. Pat. No. 4,504,465 (Sampson et al) and U.S. Pat. No. 4,617,185 (DiPietro).

Soap gel technology to achieve solid sticks has also been employed in U.S. Pat. No. 4,226,889 (Yuhas). Therein is reported an aqueous sodium stearate-water vehicle delivering an active ingredient for deposit on human skin. Among the actives are bacteriostats, fungistats, pigments, dyes, perfumes, emollients, humectants, ultraviolet absorbers, talc and insect repellants.

U.S. Pat. No. 4,702,916 (Geria) describes an analgesic stick comprising a delivery system of alcohol, soap, water and a variety of analgesic agents.

U.S. Pat. No. 3,579,465 (Schmolka) discloses preparation of transparent ringing organic polymer gels structured through use of a polyoxyethylated-polyoxypropylene glycol adduct of ethylene diamine. Deodorant actives, astringents and pesticides were said to be includable within the gel structure.

U.S. Pat. No. 3,740,421 (Schmolka) reports formation of gels through use of polyoxyethylene-polyoxypropylene block polymers providing transparent products which may incorporate antiperspirant, astringent, antiseptic and other actives.

U.S. Pat. No. 2,900,306 (Slater) is concerned with formulation of frozen colognes. Among the components required to form stick products are a solid alcohol base having dispersed therein a minor amount of a water-soluble soap. Deodorant sticks are described therein with a major amount of alcohol solidified by a minor amount of sodium stearate, a deodorant and a minor amount of a lower alkylolamine soap.

EP 0 137 173 (Graham) describes a deodorant formulation containing a lower alcohol, water and amino alkanol, such as 2-amino-2-methylpropan-1-ol. Amino alcohols were said to provide improved deodorancy and clear formulations.

U.S. Pat. No. 4,948,578 (Burger et al) describes an antiperspirant composition in the form of a transparent stick comprising a mixture of aluminum chlorohydrate, ethoxylated nonionic surfactant, a volatile silicone, an emollient oil and water.

Beyond the technical literature, there is also in public use a wide variety of translucent deodorant sticks. For instance, a typical product such as Power Stick ® lists on the package as ingredients: propylene glycol, water, sodium stearate, lauramide DEA, fragrance, Triclosan, hydroxyethylcellulose and colorants.

A problem with the known art is that the products are relatively harsh to the skin. This is especially evident with soap structured gels. When a part of the soap is replaced with another structurant such as an ethoxylated-propoxylated fatty alcohol, irritancy is reduced without compromising rigidity. However, this and other mildness-promoting ingredients have not provided the desired high degree of clarity.

Accordingly, it is an object of the present invention to provide a cosmetic stick that is mild towards the skin.

Another object of the present invention is to provide a cosmetic stick having improved clarity.

A further object of the present invention is to provide a cosmetic stick for use as a deodorant with the improved properties of lower irritation and clarity.

A still further object of the present invention to provide a cosmetic stick that does not opacify upon storage These and other objects of the present invention will become more apparent by consideration of the following summary, detailed description and examples.

SUMMARY OF THE INVENTION

A clear stick composition is provided comprising:

(i) from about 10 to about 90% of a polyhydric alcohol having from 2 to 6 carbon atoms and from 2 to 6 hydroxyl groups;

(ii) from about 1 to about 40% of a soap;

(iii) from about 1 to about 40% of an alkoxylate copolymer having the following formula:

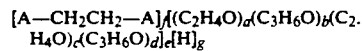

wherein

A is nitrogen;

a, b, c and d are independently selected integers ranging from 0 to 200 with the proviso that the sum of a, b, c and d is at least about 50;

e is an integer from 1 to 4;

f is an integer from 0 to 1;

g is an integer from 0 to 4; and (iv) an effective amount of a clarifying agent which is a basic amine present in an effective amount to maintain clarity of the stick.

DETAILED DESCRIPTION OF THE INVENTION

Now it has been discovered that a cosmetic stick of much improved mildness and clarity can be obtained by partially replacing soap as a structurant with a polyethylene oxide-polypropylene oxide copolymer. In combination therewith it has also been discovered that basic amines can provide a clarity stabilizing effect upon the composition.

The copolymer of the invention will be of the general structure:

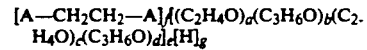

wherein

A is nitrogen;

a, b, c and d are independently selected integers ranging from 0 to 200 with the proviso that the sum of a, b, c and d is at least about 50;

e is an integer from 1 to 4;

f is an integer from 0 to 1; and
g is an integer from 0 to 4.

When f and e are 0 and 1, respectively, the structure described is a poly(ethylene oxide)(propylene oxide)-(ethylene oxide) copolymer. Typical of this substance are a series of products from the BASF Corporation sold under the Pluronic trademark. For purposes of this invention, copolymers of this type will have an average molecular weight ranging from about 5000 to about 50,000, preferably between about 6,000 and 15,000. Melt/pour points of these materials should be at least 30° C., preferably at least 50° C., and optimally at least 55° C.

Illustrative commercially available products are Pluronic F127 ® and Pluronic F108 ®.

When f is 1, the general structure defines a tetra-functional copolymer derived from the sequential addition of propylene oxide and ethylene oxide to ethylene diamine and that may be described in terms of structures (1) and (2) as follows:

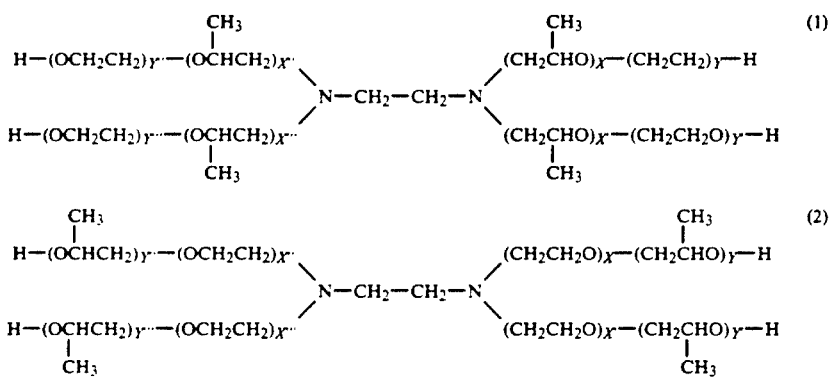

wherein X, X', X", X''', Y, Y', Y", Y''' are integers such that the average molecular weight of the copolymer ranges from about 1,500 to 100,000. Preferably, the average molecular weight should range from about 5,000 up to about 50,000, optimally between about 15,000 to about 30,000. Additionally, the copolymers are characterized by having an HLB of at least b 12, preferably between 18 and 23, optimally above 24. Best results are obtained when the copolymer has a melt-/pour point of at least 30° C., preferably greater than 40° C., optimally greater than 50° C. These structurants are commercially available from the BASF Corporation sold under the trademark, Tetronic ®. Especially suitable are Tetronic 1107, Tetronic 1307 and Tetronic 1508.

Amounts of the copolymer structurant will range anywhere from about 1 to about 40% by weight. Preferably the amount will range from about 2 to 20%, optimally between about 3 and 10% by weight.

A clarifying agent for maintaining clarity of the stick is a further advantageous component of the present invention. This agent will be a basic amine and preferably selected from amino alkanols having from 2 to 6 hydroxyl groups. These alkanols may include anywhere from about 3 to 18 carbon atoms and have molecular weights less than 1,000. Particularly effective are the propanol amines. Illustrative of this category is tetra(-hydroxypropyl) diamine available from the BASF Corporation under the trademark, Quadrol ®. Even more preferred is 2-amino-2-methylpropan-1-ol available from the Angus Chemical Company under the trademark, AMP ®. Also suitable are 2-amino-2-ethyl-1,3-propanediol available from the Angus Chemical Company under the trademark, AMPD ® and 2-amino-2-hydroxymethyl-1,3-propanediol (generically referred to as Tromethamine) available from the Sigma Chemical Company.

The basic amine of the invention will be present in amounts ranging from about 0.1 to about 20%, preferably from about 0.5 to about 5%, optimally between about 1 and 3% by weight.

Another component of compositions of the present invention will be that of a soap. The soap will be derived from $C_{12}$-$C_{22}$, preferably $C_{16}$-$C_{18}$, carbon atom fatty acids in the form of a sodium, potassium or aluminum salt.

Soaps will generally comprise from about 1 to about 40%, preferably from about 3 to about 15%, optimally between about 4 and about 10% by weight of the composition.

Fatty acids which form the soap may include myristic, palmitic, stearic, oleic, linoleic, linolinic, margaric and mixtures of such acids. Naturally occurring sources of such fatty acids include coconut oil, beef tallow, lanolin, fish oil, beeswax, palm oil, peanut oil, olive oil, cottonseed oil, soybean oil, corn oil, rapeseed, rosin acids and greases. Preferred fatty acid soaps are sodium stearate, sodium palmitate, potassium stearate, potassium palmitate, sodium myristate, aluminum monostearate and mixtures thereof.

A further component of the compositions of this invention is a polyhydric alcohol containing from 2 to 6 hydroxyl groups, preferably 2 to 3. The alcohol may also contain from 2 to 6 carbon atoms, preferably 2 to 3 carbon atoms. Suitable polyhydric alcohols include ethylene glycol, propylene glycol, trimethylene glycol, glycerin, and sorbitol. Most preferred is propylene glycol. Amounts of the polyhydric alcohol may range from about 10 to about 90%, preferably from about 40 to about 70%, optimally between about 50 and about 65% by weight of the composition.

Skin treatment active agents may also be included within the stick compositions. These agents may range in concentration anywhere from about 0.01 to about 30%, preferably from about 0.1 to about 10%, optimally between about 0.5 and 2% by weight of the composition. Within this category are included bacteriostats, fungistats, sunscreens or ultraviolet absorbers, analgesics, anti-skin wrinkle agents, colorants, astringents and antioxidants.

When the product is a deodorant stick, the active ingredient will be a bacteriostat which includes 2,2'-methylenebis(3,4,6-trichlorophenol), 2,4,4'-trichloro-2'- hydroxy(diphenyl ether), zinc phenolsulfonate, 2,2'-thiobis(4,6-dichlorophenol), p-chloro-m-xylenol, dichloro-m-xylenol and the like. Most preferred is 2,4,4'-trichloro-2'-hydroxy(diphenyl ether), which is generically known as Triclosan and available from the Ciba-Geigy Corporation under the trademark, Irgasan DP-300 ®. When Triclosan is utilized it will be present in a range from about 0.05 to about 0.9%, preferably from about 0.1 to about 0.5% by weight of the composition. Other types of bacteriostats may include sodium N-lauroyl sarcosine, sodium N-palmitoyl sarcosine, lauroyl sarcosine, N-myristoyl glycine, potassium N-lauroyl sarcosine, and aluminum chlorhydroxy lactate (sold by Reheis Chemical Company under trademark of Chloracel).

When the product is a sunscreen composition, the active ingredient may include an ultraviolet absorber such as p-aminobenzoic acid, its salts, or its esters, as well as N-substituted derivatives such as p-(dimethylamino) benzoic acid, an anthranilate, a salicylate, esters of cinnamic acid, dihydroxycinnamic acid or trihydroxycinnamic acid, diphenyl-butadiene, stilbene, a napthol sulfonate, a coumarin derivative, a quinine salt, a quinoline derivative, hydroquinone, tannic acid, zinc oxide, polyethylene particles, titanium dioxide particles, iron oxide particles, dioxybenzone and oxybenzone. Amounts of the ultraviolet absorber may range from about 0.5 to about 5%, preferably from about 1 to 4% by weight of the total composition.

When the composition is a makeup stick in which a solid pigment is to be applied as a rouge, lipstick, eyeshadow or eyeliner, the active ingredient may include titanium dioxide, zinc oxide, iron oxide, aluminum lake, barium lake, calcium lake, strontium lake, tetrabromofluorescein, tetrabromotetrachlorofluorescein, dibromofluorescein and the like. Amounts of the pigment may range from about 1 to about 10%, preferably from about 3 to about 8% by weight of the total composition.

When the product is an anti-skin wrinkle composition, the active ingredient may include Ceramides, 2-hydroxyoctanoic acid, retinoic acid, retinol, esters of retinol and retinoic acid, and mixtures thereof. Amounts of the anti-skin wrinkle active ingredient may range from as little as 0.0001 to about 5%, preferably between about 0.001 and about 1% by weight of the composition.

Water is an important component of the compositions of the present invention. Water will generally be present in amounts ranging from about 10 to about 60%, preferably from about 15 to about 40%, optimally between about 25 and 30% by weight.

A variety of optional components may also be present in the compositions of this invention. These optional ingredients may include an emollient. Typical emollients that may be employed are fatty esters, fatty ethers, alkoxylated fatty esters, fatty alcohols and low molecular weight silicone fluids. Specific emollient examples include isopropyl palmitate, cetyl alcohol, stearyl alcohol, diisopropyl adipate, dimethicone copolyol, cyclomethicone, dimethicone, alkoxylated sugar derivatives such as alkyl polyglycosides and combinations thereof. Amounts of the emollient may range anywhere from about 1 to about 40%, preferably from about 5 to about 25% by weight.

The term "clear" as used in this specification is intended to connote its usual dictionary definition. Thus, a clear cosmetic stick, like glass, allows for ready viewing of objects behind it. By contrast, a translucent cosmetic stick, although allowing light to pass through, causes the light to be so scattered that it will be impossible to clearly identify objects behind the translucent stick.

Within the context of this invention, a cosmetic stick is deemed to be clear if the maximum transmittance of light of any wavelength in the range 400 to 900 nm through a sample 1 cm thick is greater than 35%, but preferably at least 60%. A stick is deemed translucent if the maximum transmittance of such light through the sample is between 2% and less than 35%. Finally, a stick is deemed opaque if the maximum transmittance of such light is less than 2%. This transmittance can be easily measured by placing a stick sample of the required thickness into the light beam path of a UV-VIS spectrophotometer such as a Bausch & Lomb Spectrophotometer.

The following examples will more fully illustrate the embodiments of this invention. All parts, percentages and proportions referred to herein and in the appended claims are by weight unless otherwise indicated.

EXAMPLE 1

A series of sticks were formulated to evaluate the relative effect of various amine bases and of various alkoxylated copolymers. The test compositions are outlined in Table I.

TABLE I

| Ingredients | Formulation (Wt. %) | | | |
|---|---|---|---|---|
| | A | B | C | D |
| Propylene Glycol | 61.50 | 60.00 | 60.00 | 62.00 |
| Deionized Water | 27.05 | 27.05 | 27.05 | 27.05 |
| Sodium Stearate | 5.50 | 5.50 | 5.50 | 5.50 |
| Alkoxylated Copolymer | 4.00 | 4.00 | 4.00 | 4.00 |
| Irgasan DP-300 | 0.30 | 0.30 | 0.30 | 0.30 |
| Amine Base | 0.50 | 2.00 | 2.00 | — |
| Fragrance | 1.00 | 1.00 | 1.00 | 1.00 |
| Red Color | 0.15 | 0.15 | 0.15 | 0.15 |

Each of the above sticks were evaluated for light transmittance and then placed in an oven for accelerated aging studies at temperatures of 70° F., 100° F., 110° F., and 120° F. Results of these experiments are reported in Table II.

TABLE II

| Formula | Alkoxylated Polymer | Amine Base | Transmittance Analysis | | | | | | | | |
|---|---|---|---|---|---|---|---|---|---|---|---|
| | | | Initial Trans (%) | Two Week Storage (°F.)* | | | | One Month Storage (°F.)* | | | |
| | | | | 70 | 100 | 110 | 120 | 70 | 100 | 110 | 120 |
| A | F-127 | AMP | 83 | 85 | 77 | 51 | 68 | 80 | 76 | 73 | 68 |
| B | F-127 | QUADROL | 78 | 81 | 79 | 76 | 71 | 80 | 79 | 73 | 72 |
| C | F-127 | MONAMID 716 | 77 | 79 | 74 | 71 | 57.5 | 78 | 74 | 70 | 2 |
| D | F-127 | — | 75 | 77 | 5 | 1 | 0.5 | 40 | 1 | 0 | 0 |
| A | T-1307 | AMP | 75 | 77 | 66 | 61 | 63 | 76 | 75 | 70 | 60 |
| B | T-1307 | QUADROL | 77 | 79 | 79 | 75 | 65 | 79 | 78 | 60 | 6 |
| C | T-1307 | MONAMID 716 | 76 | 77 | 74 | 71 | 69 | 76 | 15 | 18 | 3 |
| D | T-1307 | — | 71 | 73 | 8 | 1 | 1 | 65 | 2 | 0 | 0 |

TABLE II-continued

| Formula | Alkoxylated Polymer | Amine Base | Transmittance Analysis | | | | | | | | |
|---|---|---|---|---|---|---|---|---|---|---|---|
| | | | Initial Trans (%) | Two Week Storage (°F.)* | | | | One Month Storage (°F.)* | | | |
| | | | | 70 | 100 | 110 | 120 | 70 | 100 | 110 | 120 |
| A | T-1508 | AMP | 78 | 71 | 82 | 79 | 26 | 78 | 76 | 75 | 61 |
| B | T-1508 | QUADROL | 80 | 83 | 50 | 80 | 42 | 65 | 70 | 80 | 11 |
| C | T-1508 | MONAMID 716 | 81 | 83 | 80 | 67 | 4 | 82 | 24 | 4 | 3 |
| D | T-1508 | — | 72 | 74 | 6 | 2 | 1 | 70 | 6 | 1 | 1 |
| A | TRITON X-100 | AMP | 37 | 37 | 34 | 34 | 52 | 32 | 30 | 36 | 55 |
| B | TRITON X-100 | QUADROL | 55 | 55 | 57 | 54 | 60 | 55 | 55 | 53 | 14 |
| C | TRITON X-100 | MONAMID 716 | 46 | 45 | 45 | 48 | 14 | 40 | 40 | 5 | 2 |
| D | TRITON X-100 | — | 51 | 52 | 8 | 2 | 1 | 48 | 1 | 0 | 0 |

*Percent Transmittance

From Table II it is evident that lauryl diethanolamides such as Monamid 716 are not effective for retaining long-term clarity under conditions of aging. On the other hand, AMP® and Quadrol® generally provided much better storage stability. Especially effective was AMP®which, at 120° F. storage for one month, allowed 60% or higher transmittance to be retained. For purposes of this invention, a transmittance of 60% or higher at 120° F. for one month is considered to be a satisfactory result.

Not all alkoxylated polymers perform well with respect to clarity. Triton X-100®, an ethoxylated phenol, was found to be substantially inferior to the alkoxylated copolymers identified as Pluronic F-127®, Tetronic T-1307® and T-1508®.

EXAMPLE 2

A series of comparative experiments were performed to evaluate the effect of alkoxylate polymers that contain a hydrophobe moiety, such as a $C_{12}$–$C_{20}$ fatty acid or alcohol residue, serving as an anchoring unit in the polymer. Specific examples of such hydrophobe-containing polymers are PPG-3 Myristyl Ether and PPG-5 Ceteth-20 which contain the respective hydrophobe groups of myristyl alcohol and cetearyl alcohol. U.S. Pat. No. 4,759,924 (Luebbe et al) describes a formulation under Example 1 describing a "clear" stick employing the aforementioned polymers. Table III lists this formulation (D) and variations thereof further containing various neutralizing bases.

TABLE III

Comparative Experiments with Hydrophobe Polymers

| Ingredients | Formulation (Wt. %) | | | |
|---|---|---|---|---|
| | A | B | C | D |
| Propylene Glycol | 56.10 | 54.60 | 54.60 | 56.60 |
| Deionized Water | 29.65 | 29.65 | 29.65 | 29.65 |
| PPG-3 Myristyl Ether | 2.50 | 2.50 | 2.50 | 2.50 |
| PPG-5 Ceteth-20 | 3.00 | 3.00 | 3.00 | 3.00 |
| Sodium Stearate | 6.80 | 6.80 | 6.80 | 6.80 |
| Irgasan DP-300 | 0.30 | 0.30 | 0.30 | 0.30 |
| AMP | 0.50 | — | — | — |
| Quadrol | — | 2.00 | — | — |
| Monamid 716 | — | — | 2.00 | — |
| Fragrance | 1.00 | 1.00 | 1.00 | 1.00 |

TABLE III-continued

Comparative Experiments with Hydrophobe Polymers

| Ingredients | Formulation (Wt. %) | | | |
|---|---|---|---|---|
| | A | B | C | D |
| Colorant | 0.15 | 0.15 | 0.15 | 0.15 |

A series of transmittance tests were performed on sticks resulting from the formulations of Table III. These sticks were evaluated for clarity initially and also after storage for two weeks and one month at 70° F., 100° F., and 120° F. Results are listed in Table IV.

TABLE IV

| Formula | Alkoxylated Polymer (PPG-3-Myristyl Ether/PPG-5-Ceteth-20) | Amine Base | Comparative Transmittance Results | | | | | | | | |
|---|---|---|---|---|---|---|---|---|---|---|---|
| | | | Initial Trans (%) | Two Week Storage (°F.)* | | | | One Month Storage (°F.)* | | | |
| | | | | 70 | 100 | 110 | 120 | 70 | 100 | 110 | 120 |
| A | LUEBBE | AMP | 49 | 49 | 27 | 46 | 54 | 47 | 40 | 35 | 29 |
| B | LUEBBE | QUADROL | 46 | 47 | 44 | 43 | 47 | 49 | 34 | 25 | 56 |
| C | LUEBBE | MONAMID 716 | 50 | 52 | 55 | 54 | 4 | 52 | 47 | 48 | — |
| D | LUEBBE | — | 41 | 42 | 43 | 3 | 1 | 40 | 3 | 1 | 0 |
| E | NONE | — | 5 | 3 | 1 | 1 | 1 | 1 | 1 | 0 | 0 |

*Percent Transmittance

From the results of Table IV it is evident that the presence of a hydrophobe in the alkoxylated polymer does not achieve the minimum of 60% transmittance either initially or after storage. To be noted, however, is that the presence of a basic amine does significantly improve clarity over the formula in Example 1 of the prior art and importantly maintains such clarity over time.

EXAMPLE 3

Relative irritancy of a series of deodorant sticks was evaluated using a modification of a the Cumulative Irritation Assay described by Lanman, B. M., Elvers, W. B. and Howard, C. S., "The Role of Human Patch Testing in Product Development Program", Proceedings, Joint Conference on Cosmetic Sciences, pp. 135-145, The Toilet Goods Assoc., Inc., 1968.

A total of twenty-one (21) subjects ranging in age from 18 to 65 years were empaneled. The subjects were first ascertained as not exhibiting any physical or dermatological conditions which would have interfered with the purpose or integrity of the study.

The amount of each test sample applied to a respective patch was approximately 0.2 g solids in 0.2 ml of a liquid carrier. These samples were then placed onto a Park-Davis Readi-Bandage® occlusive patch, which was applied to the back of each subject between the scapulae and waist, adjacent to the spinal midline.

Days 1 to 14 (Cumulative Irritation Phase)

The patches were worn for 14 consecutive days. Freshly prepared patches were applied to the same test site Monday through Saturday. Patches applied on Saturday were worn until Monday (48-hour contact). They were then removed approximately twenty-four (24) hours after each application and visually scored for irritation reactions just prior to the next patch application. Readings for Sunday were recorded as being the same as those observed on Monday. The following 6-point dermal scoring scale was used:

0 = No evidence of any effect
+ = Barely Perceptible (minimal, faint, uniform or spotty erythema)
1 = Mild (pink, uniform erythema covering most of the contact site)
2 = Moderate (pink-red erythema uniform in the entire contact site)
3 = Marked (bright-red erythema with/without petechiae or papules)
4 = Severe (deep-red erythema with/without vesiculation or weeping)

Accompanying edema (swelling) at any test site was recorded with an "e" and described as mild, moderate or severe.

All panelists were instructed to keep the patch test areas as dry as possible while showering or bathing during the course of the study.

Patch sites were evaluated daily and recorded on a Cumulative Irritation Patch Test recording form. Individual test article scores were calculated via summation of the results for each day. The maximum irritation severity score was 4. For panelist safety reasons, however, if a dermal reaction of 3 or 4 occurred at any point during the study, further patch testing on that subject, at the test site involved was terminated and the 3-level or 4-level score was assigned to that site for the subsequent scheduled test days.

Any subject who missed an observation day was required to keep their patches in place until their next scheduled visit to the Clinic. The score assigned on this day was also used for the previously missed observation day.

Day 15 to 26 (Rest Phase)

An approximate 2-week "rest" phase followed removal of the final cumulative irritation patches. No exposure to the patch test materials was made during this phase.

Day 26 to 29 (Challenge Phase)

A "Challenge" patch of each test article was applied to a virgin test site on the back. The Challenge patches were removed and scored 24 hours later and scored again 72 hours post-application, using the same scoring criteria previously described.

Table V lists the samples evaluated in the Cumulative Irritation Assay.

TABLE V

Sample Compositions

| Ingredient | Formulation (Wt. %) | | | | | | |
|---|---|---|---|---|---|---|---|
| | A | B | C | D | E | F | G |
| Propylene Glycol | 60.0 | 61.36 | 61.87 | 60.86 | 60.86 | 59.36 | 59.36 |
| Deionized Water | 26.945 | 26.945 | 26.945 | 26.945 | 26.945 | 26.945 | 26.945 |
| Sodium Stearate | 7.5 | 5.5 | 5.5 | 6.0 | 6.0 | 7.5 | 7.5 |
| Pluronic F127 | — | 4.0 | 4.0 | — | — | — | — |
| Tetronic 1508 | — | — | — | 4.0 | — | — | — |
| Tetronic 1107 | — | — | — | — | 4.0 | — | — |
| Brij 58 | — | — | — | — | — | 4.0 | — |
| Triton X-100 | — | — | — | — | — | — | 4.0 |
| Irgasan DP-300 | 0.3 | 0.3 | 0.3 | 0.3 | 0.3 | 0.3 | 0.3 |
| Neutrol TE | — | 0.64 | — | 0.64 | 0.64 | 0.64 | 0.64 |
| Monamid 716 | 4.0 | — | — | — | — | — | — |
| Colorants (0.5% active) | 0.15 | 0.15 | 0.15 | 0.15 | 0.15 | 0.15 | 0.15 |
| Fragrance | 1.0 | 1.0 | 1.0 | 1.0 | 1.0 | 1.0 | 1.0 |
| Sodium Meta Bisulphite | 0.1 | 0.1 | 0.1 | 0.1 | 0.1 | 0.1 | 0.1 |

Additionally evaluated were Sample H, which was a commercial Baby Oil, and Sample I, which was a 0.1% solution of sodium lauryl sulfate, both utilized as control samples.

Results of the 14-day Cumulative Irritancy Test with Challenge are reported in Table VI.

TABLE VI

Irritancy Test Results

| Formulation No. | Total Cumulative Irritancy Scores* | Total Cumulative Irritancy Scores** |
|---|---|---|
| I | 496.5 | 23.6 |
| F | 394.5 | 18.8 |
| A | 296.5 | 14.1 |
| G | 260.0 | 12.4 |
| C | 189.5 | 9.0 |
| B | 182.5 | 8.7 |
| E | 177.0 | 8.4 |
| D | 155.5 | 7.4 |
| H (Baby Oil) | 13.5 | 0.6 |

*Highest possible TOTAL irritancy score = 1,176 (21 subjects × 14 days × "4").
**Highest possible MEAN irritancy score = 56 (1,176 ÷ 21 subjects).

The test results were ranked in Table VI based on highest to lowest cumulative irritations. There was no evidence of induced allergic contact dermatitis in the subjects.

Sample A is representative of commercially available deodorant sticks. As can be seen from the results with Samples B, C, D and E, incorporation of a Pluronic or Tetronic alkoxylate very significantly reduces irritancy relative to Sample A.

By contrast, incorporation of Brij 58 and Triton X-100 in Samples F and G do not provide any significant improvement with irritancy. Comparison of Samples B and C with that of E and D indicates somewhat improved irritancy scores by changing from Pluronic to Tetronic-type alkoxylates.

The foregoing description and examples illustrate selected embodiments of the present invention and in light thereof variations and modifications will be suggested to one skilled in the art, all of which are in the spirit and purview of this invention.

What is claimed is:

1. A clear stick composition having a light transmittance of at least 60% after one-month storage at 120° F., said composition comprising:
   (i) from about 10 to about 90% of a polyhydric alcohol having from 2 to 6 carbon atoms and from 2 to 6 hydroxyl groups;
   (ii) from about 1 to about 40% of a soap which is a $C_{12}-C_{22}$ fatty acid salt;
   (iii) from about 1 to about 40% of an alkoxylate copolymer having the following formula:

$$[A-CH_2CH_2-A]_f[(C_2H_4O)_a(C_3H_6O)_b(C_2H_4O)_c(C_3H_6O)_d]_e[H]_g$$

wherein
   A is nitrogen;
   a, b, c and d are independently selected integers ranging from 0 to 200 with the proviso that the sum of a, b, c and d is at least about 50;
   e is an integer from 1 to 4;
   f is an integer from 0 to 1;
   g is an integer from 0 to 4; and
   when f is 1 then said copolymer has a molecular weight from about 15,000 to about 50,000 and when f is 0 said copolymer having a molecular weight from about 5,000 to about 50,000; and
   (iv) a clarifying agent which is a basic amine that is an amino alkanol having from 2 to 6 hydroxyl groups, said clarifying agent being present in an effective amount to maintain clarity of said stick.

2. The composition according to claim 1, wherein the amine is present in an amount from about 0.1 to about 20% by weight.

3. The composition according to claim 1, wherein the amine is present in an amount from about 0.5 to about 5% by weight.

4. The composition according to claim 1, wherein the amine is an amino alcohol having a molecular weight less than 1000.

5. The composition according to claim 1, wherein the amine is an amino alcohol selected from the group consisting of 2-amino-2-methylpropan-1-ol, 2-amino-2-ethyl-1,3-propanediol, tetra(hydroxypropyl)diamine, 2-amino-2-hydroxymethyl-1,3-propanediol and mixtures thereof.

6. The composition according to claim 1, wherein the copolymer is a tetra-functional block copolymer derived from the addition of propylene oxide and ethylene oxide to ethylene diamine.

7. The composition according to claim 1 wherein said clarifying agent is present in an amount from about 0.1 to 3% by weight.

8. The composition according to claim 1, wherein the copolymer is a block copolymer formed solely of propylene oxide and ethylene oxide.

9. The composition according to claim 8, wherein the block copolymer is formed of alternating blocks of poly(ethylene oxide), poly(propylene oxide) and poly(ethylene oxide).

10. The composition according to claim 1, wherein the copolymer is formed from the sequential addition of propylene oxide and ethylene oxide to ethylene diamine.

11. The composition according to claim 1, further comprising an active ingredient selected from the group consisting of bacteriostats, fungistats, sunscreens, antiskin wrinkling agents, colorants, antiperspirants and combinations thereof.

12. The composition according to claim 11 wherein the active ingredient opacifies the clear stick composition.

13. A cosmetic stick composition comprising:
   (i) from about 10 to about 90% of a polyhydric alcohol having from 2 to 6 carbon atoms and from 2 to 6 hydroxyl groups;
   (ii) from about 1 to about 40% of a soap which is a $C_{12}-C_{22}$ fatty acid salt;
   (iii) from about 1 to about 40% of an alkoxylate copolymer which is a tetra-functional copolymer derived from the sequential addition of propylene oxide and ethylene oxide to ethylene diamine having a structure selected from the group consisting of:

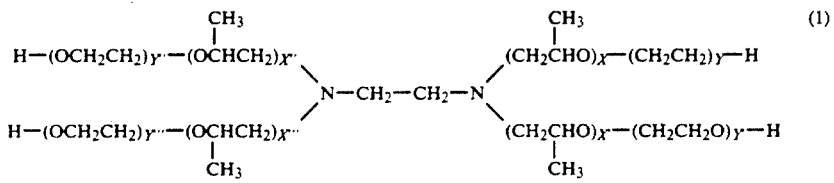

and

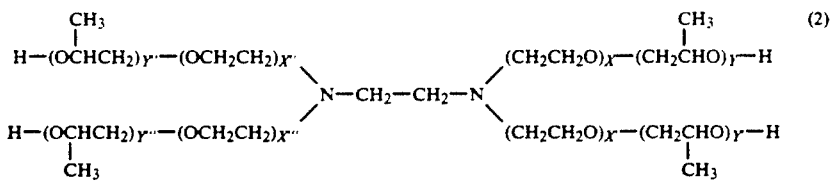

wherein X, X', X'', X''', Y, Y', Y'', Y''' are integers such that the average molecular weight of the copolymer ranges from about 15,000 to 50,000.

14. The composition according to claim 1 further comprising water in an amount from about 10 to about 60% by weight.

15. A clear stick composition having a light transmittance of at least 60% after one-month storage at 120° F., said composition comprising:
   (i) from about 10 to about 90% of a polyhydric alcohol having from 2 to 6 carbon atoms and from 2 to 6 hydroxyl groups;
   (ii) from about 1 to about 40% of a soap which is a $C_{12}-C_{22}$ fatty acid salt;
   (iii) from about 1 to about 40% of an alkoxylate copolymer which is a tetra-functional copolymer derived from the sequential addition of propylene oxide and ethylene oxide to ethylene diamine having a structure selected from the group consisting of:

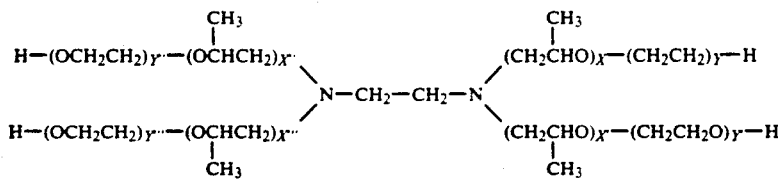

and

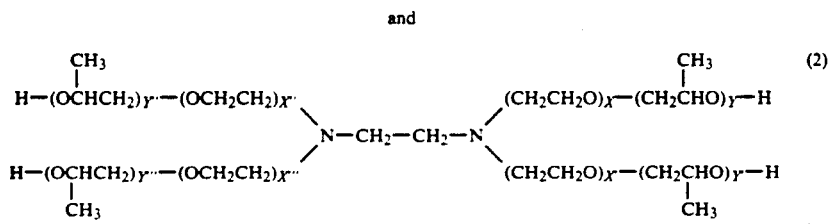

wherein X, X', X'', X''', Y, Y', Y'', Y''' are integers such that the average molecular weight of the copolymer ranges from about 15,000 to 50,000.

(iv) from about 0.1 to 3% of a clarifying agent which is an amino alcohol selected from the group consisting of 2-amino-2-methylpropan-1-ol, 2-amino-2-ethyl-1,3-propanediol, 2-amino-2-hydroxymethyl-1,3-propanediol and mixtures thereof.

16. The composition according to claim 15 wherein the amino alcohol is 2-amino-2-methylpropan1-ol.

* * * * *